United States Patent
Marshall et al.

(10) Patent No.: US 12,144,979 B2
(45) Date of Patent: *Nov. 19, 2024

(54) EXTRAVASCULAR LEAD DESIGNS FOR OPTIMIZED PACING AND SENSING HAVING SEGMENTED, PARTIALLY ELECTRICALLY INSULATED DEFIBRILLATION COILS

(71) Applicant: Medtronic, Inc., Minneapolis, MN (US)

(72) Inventors: Mark T. Marshall, Forest Lake, MN (US); Amy E. Thompson-Nauman, Ham Lake, MN (US); Melissa G. T. Christie, Andover, MN (US); Gonzalo Martinez, Mendota Heights, MN (US); Kevin R. Seifert, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 376 days.

This patent is subject to a terminal disclaimer.

(21) Appl. No.: 16/990,321

(22) Filed: Aug. 11, 2020

(65) Prior Publication Data

US 2020/0368519 A1 Nov. 26, 2020

Related U.S. Application Data

(63) Continuation of application No. 14/695,167, filed on Apr. 24, 2015, now Pat. No. 10,765,858.

(Continued)

(51) Int. Cl.
*A61N 1/05* (2006.01)
*A61N 1/39* (2006.01)

(52) U.S. Cl.
CPC .......... *A61N 1/0504* (2013.01); *A61N 1/0563* (2013.01); *A61N 1/3918* (2013.01)

(58) Field of Classification Search
CPC ... A61N 1/0504; A61N 1/3918; A61N 1/0563
See application file for complete search history.

(56) References Cited

U.S. PATENT DOCUMENTS

| 3,496,932 A | 2/1970 | Prisk et al. |
| 4,030,509 A | 6/1977 | Heilman et al. |

(Continued)

FOREIGN PATENT DOCUMENTS

| CN | 101039717 A | 9/2007 |
| CN | 103394158 A | 8/2016 |

(Continued)

OTHER PUBLICATIONS

Ganapathy et al., "Implantable Device to Monitor Cardiac Activity with Sternal Wires," Pace, vol. 37, Dec. 2014, 11 pages.

(Continued)

*Primary Examiner* — William J Levicky
(74) *Attorney, Agent, or Firm* — Shumaker & Sieffert, P.A.

(57) ABSTRACT

A lead body having a defibrillation electrode positioned along a distal portion of the lead body is described. The defibrillation electrode includes a plurality of electrode segments spaced a distance apart from each other. At least one of the plurality of defibrillation electrode segments includes at least one coated portion and at least one uncoated portion. The at least one coated portion is coated with an electrically insulating material configured to prevent transmission of a low voltage signal (e.g., a pacing pulse) while allowing transmission of a high voltage signal (e.g., a cardioversion defibrillation shock). The at least one uncoated portion is configured to transmit both low voltage (Continued)

and high voltage signals. The lead may also include one or more discrete electrodes proximal, distal or between the defibrillation electrode segments.

20 Claims, 7 Drawing Sheets

Related U.S. Application Data

(60) Provisional application No. 62/089,603, filed on Dec. 9, 2014, provisional application No. 62/075,376, filed on Nov. 5, 2014.

(56) References Cited

U.S. PATENT DOCUMENTS

| | | | |
|---|---|---|---|
| 4,161,952 A | | 7/1979 | Kinney et al. |
| 4,336,811 A | | 6/1982 | Beck et al. |
| 4,355,646 A | | 10/1982 | Kallok et al. |
| 4,628,934 A | | 12/1986 | Pohndorf et al. |
| 4,760,852 A | | 8/1988 | Lekholm |
| 4,765,341 A | | 8/1988 | Mower et al. |
| 4,784,161 A | * | 11/1988 | Skalsky ............... A61N 1/0565 607/116 |
| 4,922,927 A | | 5/1990 | Fine et al. |
| 4,947,866 A | | 8/1990 | Lessar et al. |
| 4,991,603 A | | 2/1991 | Cohen et al. |
| 5,174,288 A | | 12/1992 | Bardy et al. |
| 5,176,135 A | | 1/1993 | Fain et al. |
| 5,282,845 A | | 2/1994 | Bush et al. |
| 5,325,870 A | | 7/1994 | Kroll et al. |
| 5,336,253 A | | 8/1994 | Gordon et al. |
| 5,342,414 A | | 8/1994 | Mehra |
| 5,456,706 A | | 10/1995 | Pless et al. |
| 5,476,502 A | | 12/1995 | Rubin |
| 5,522,874 A | | 6/1996 | Gates |
| 5,531,782 A | | 7/1996 | Kroll et al. |
| 5,534,022 A | * | 7/1996 | Hoffmann ............ A61N 1/0563 607/122 |
| 5,545,205 A | | 8/1996 | Schulte et al. |
| 5,654,030 A | | 8/1997 | Munshi et al. |
| 5,662,697 A | | 9/1997 | Li et al. |
| 5,676,694 A | | 10/1997 | Boser et al. |
| 5,683,443 A | | 11/1997 | Munshi et al. |
| 5,800,465 A | | 9/1998 | Thompson et al. |
| 5,810,887 A | | 9/1998 | Accorti, Jr. et al. |
| 5,833,714 A | | 11/1998 | Loeb |
| 5,849,031 A | | 12/1998 | Martinez et al. |
| 5,916,243 A | | 6/1999 | KenKnight et al. |
| 6,256,541 B1 | | 7/2001 | Heil et al. |
| 6,278,897 B1 | | 8/2001 | Rutten et al. |
| 6,327,498 B1 | | 12/2001 | Kroll |
| 6,345,198 B1 | | 2/2002 | Mouchawar et al. |
| 6,658,289 B2 | | 12/2003 | Helland |
| 6,721,598 B1 | | 4/2004 | Helland et al. |
| 6,760,619 B1 | * | 7/2004 | Helland ............... A61N 1/3684 607/4 |
| 7,108,549 B2 | | 9/2006 | Lyu et al. |
| 7,236,828 B2 | | 6/2007 | Casavant et al. |
| 7,668,601 B2 | | 2/2010 | Hegland et al. |
| 7,761,150 B2 | | 7/2010 | Ghanem et al. |
| 7,848,806 B1 | | 12/2010 | Kroll |
| 7,917,216 B1 | | 3/2011 | Ryu et al. |
| 8,017,179 B2 | | 9/2011 | Atanasoka et al. |
| 9,468,754 B2 | | 10/2016 | Martinez et al. |
| 9,855,419 B2 | | 1/2018 | Laske et al. |
| 10,765,858 B2 | * | 9/2020 | Marshall ............... A61N 1/0504 |
| 2004/0127966 A1 | | 7/2004 | Frericks et al. |
| 2005/0131509 A1 | * | 6/2005 | Atanassoska ........ A61N 1/0565 607/122 |
| 2005/0221671 A1 | | 10/2005 | Lyu et al. |
| 2006/0020316 A1 | | 1/2006 | Martinez et al. |
| 2006/0161206 A1 | | 7/2006 | Efimov et al. |
| 2007/0250142 A1 | | 10/2007 | Francis et al. |
| 2008/0004670 A1 | | 1/2008 | McVenes et al. |
| 2008/0090399 A1 | * | 4/2008 | Malik ............... A61N 1/0565 438/597 |
| 2008/0195163 A1 | | 8/2008 | Scharmer |
| 2009/0248117 A1 | | 10/2009 | Nippoldt et al. |
| 2009/0249117 A1 | | 10/2009 | Horikoshi |
| 2009/0264780 A1 | | 10/2009 | Schilling |
| 2009/0287266 A1 | | 11/2009 | Zdeblick |
| 2010/0198284 A1 | | 8/2010 | Zhou et al. |
| 2010/0305675 A1 | * | 12/2010 | Laske ............... A61N 1/0534 607/116 |
| 2013/0023944 A1 | | 1/2013 | Doerr |
| 2014/0052120 A1 | | 2/2014 | Benscoter et al. |
| 2014/0109404 A1 | | 4/2014 | Arnholt |
| 2016/0121106 A1 | | 5/2016 | Marshall et al. |

FOREIGN PATENT DOCUMENTS

| | | |
|---|---|---|
| JP | 2009240540 A | 10/2009 |
| JP | 2013208182 A | 10/2013 |
| WO | 2005046789 A1 | 5/2005 |
| WO | 2009006331 A1 | 1/2009 |
| WO | 2010051385 A1 | 5/2010 |
| WO | 2010138533 A1 | 12/2010 |
| WO | 2013162713 A1 | 10/2013 |

OTHER PUBLICATIONS

Guenther et al., "Substernal Lead Implantation: A Novel Option to Manage OFT Failure in S-ICD patients," Clinical Research Cardiology, Published On-line Oct. 2, 2014, 3 pages.

Hayashi, et al., "Virtual Electrodes and the Induction of Fibrillation in Langendorff-Perfused Rabbit Ventricles: The Role of Intracellular Calcium", Am J Physiol Heart Circ Phsiol, Aug. 2008, 27 pages.

Hideki Hayashi, MD et al., Virtual Electrodes and the Induction of Fibrillation in Langendorft-Perfused Rabbit Ventricles: The Role of Intracellular Calcium, Am J Physiol Heart Circ Physiol (Aug. 1, 2008), Title Page, pp. 2-20, Figures (7 pages).

Marshall et al., "Extravascular Lead Designs for Optimized Pacing and Sensing Having Segmented, Partially Electrically Insulated Defibrillation Coils," CN Application No. 201580060435.8, filed Nov. 2, 2015, First Office Action Dispatched Sep. 2, 2019, 10 pages.

O'Callaghan et al., "Current Status of Implantable Cardioverter-Defibrillators", Current Problems in Cardiology, vol. 22, No. 12, Dec. 1997, 66 pages.

Tung et al., "Initial Experience Of Minimal Invasive Extra Cardiac Placement Of High Voltage Defibrillator Leads," Canadian Cardiovascular Congress 2007, Oct. 2007, vol. 23, Supplement SC, Abstract 0697, http://www.pulsus.com/ccc2007/abs/0697.htm, 2 pages.

PCT Notification of Transmittal of the International Search Report and the Written Opinion of the International Searching Authority, Mailed Apr. 7, 2016, 12 pages.

Prosecution History from U.S. Appl. No. 14/695,167, dated Nov. 15, 2016 through Jul. 2, 2020, 43 pp.

First Office Action and Search Report, and translation thereof, from counterpart Chinese Application No. 202110677847.3 dated Jan. 31, 2024, 19 pp.

Geng et al., "Pacing sites and modes in cardiac rescynchronization therapy", Journal of Zhejiang University (Medical Sciences);, vol. 38, No. 1, China Academic Journal Electronic Publishing House, Jan. 1, 2009, pp. 107-112, Translation provided for only the Abstract.

* cited by examiner

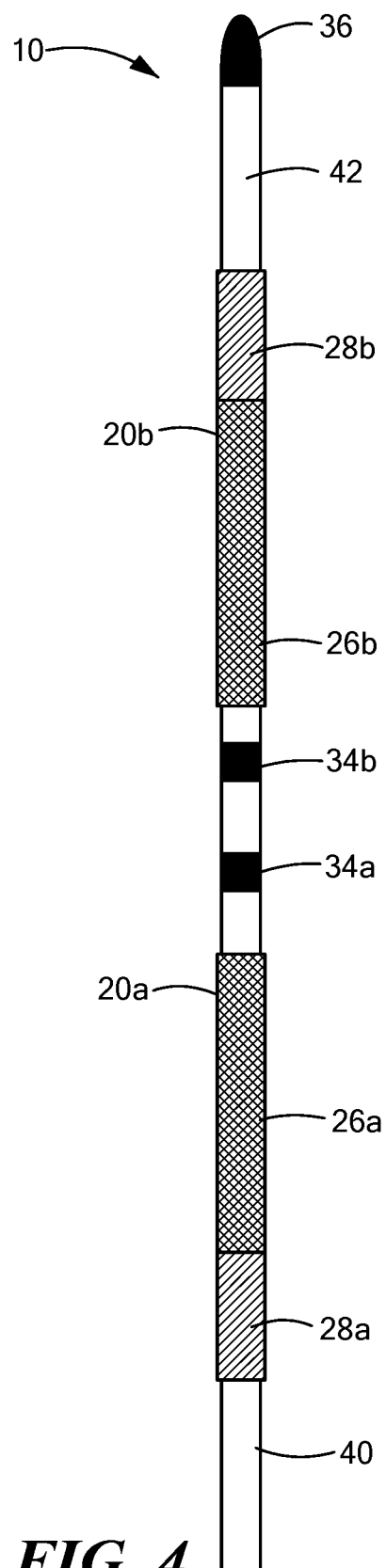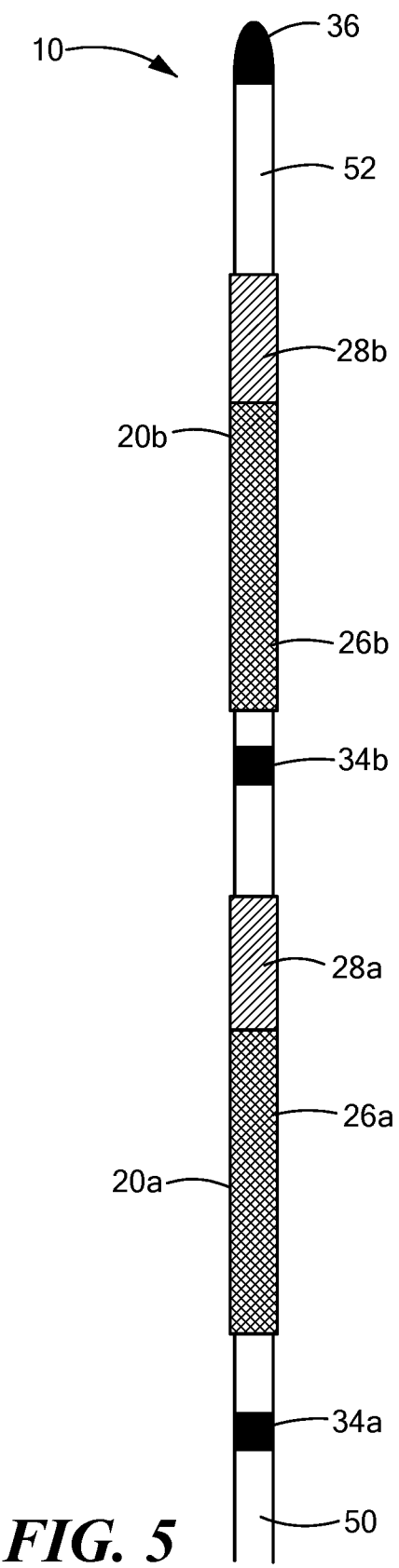

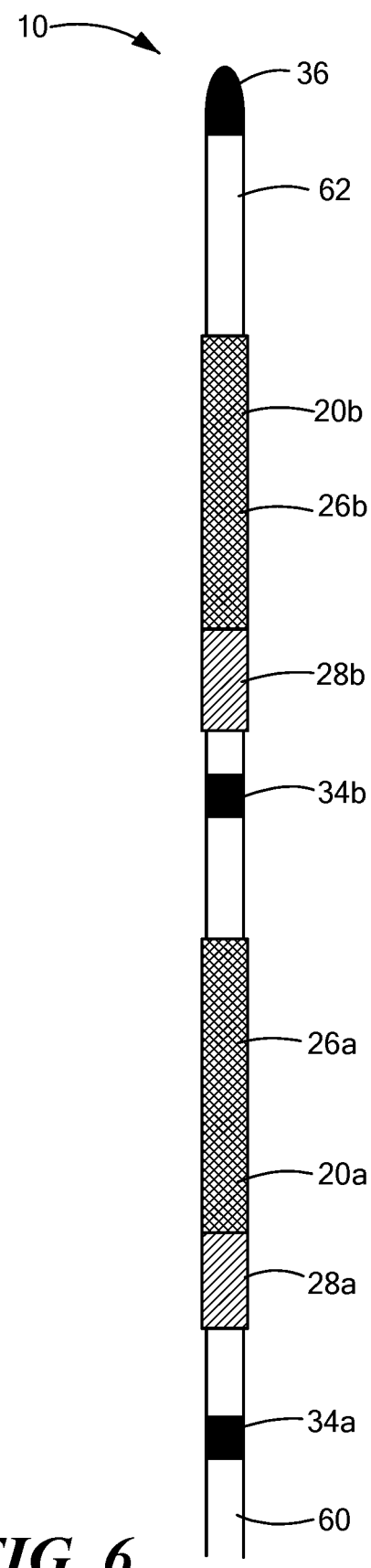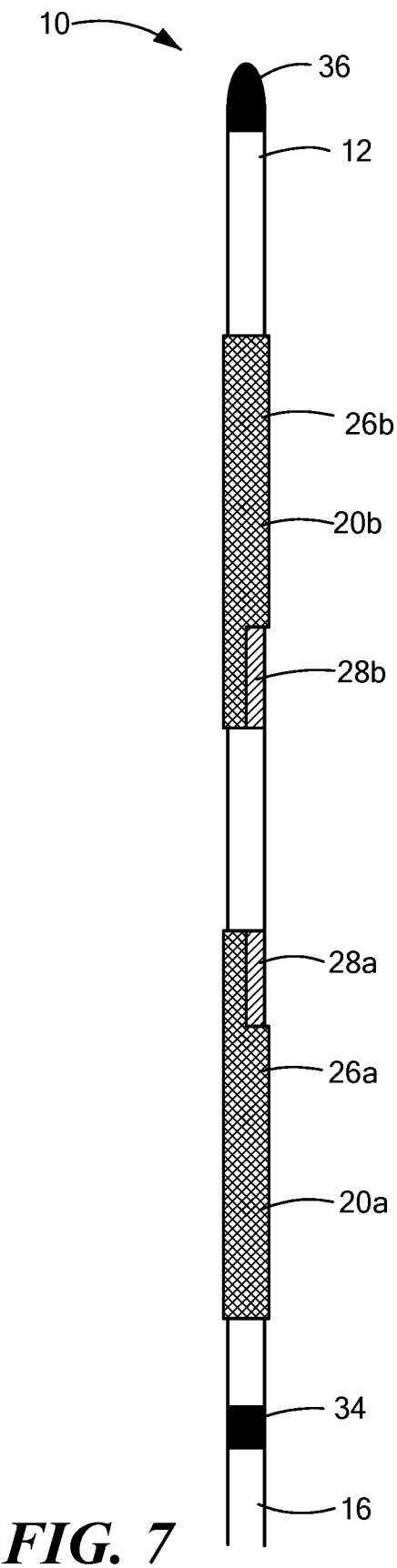
*FIG. 6*  *FIG. 7*

EXTRAVASCULAR LEAD DESIGNS FOR OPTIMIZED PACING AND SENSING HAVING SEGMENTED, PARTIALLY ELECTRICALLY INSULATED DEFIBRILLATION COILS

This application is a continuation of U.S. patent application Ser. No. 14/695,167, filed on Apr. 24, 2015, which claims the benefit of: U.S. Provisional Patent Application No. 62/089,603, filed on Dec. 9, 2014; and U.S. Provisional Patent Application No. 62/075,376 filed on Nov. 5, 2014. The entire content of each of these applications is incorporated herein by reference.

TECHNICAL FIELD

The present application relates to electrical stimulation leads and, more particularly, electrical stimulation leads with improved defibrillation, sensing, and/or pacing capability for use in extravascular and/or extracardiac, e.g., subcutaneous or substernal, applications.

BACKGROUND

Malignant tachyarrhythmia, for example, ventricular fibrillation, is an uncoordinated contraction of the cardiac muscle of the ventricles in the heart, and is the most commonly identified arrhythmia in cardiac arrest patients. If this arrhythmia continues for more than a few seconds, it may result in cardiogenic shock and cessation of effective blood circulation. As a consequence, sudden cardiac death (SCD) may result in a matter of minutes.

In patients at high risk of ventricular fibrillation, the use of an implantable cardioverter-defibrillator (ICD) system has been shown to be beneficial at preventing SCD. An ICD system includes an ICD, which is a battery powered electrical shock device, that may include an electrical housing electrode (sometimes referred to as a can electrode), that is coupled to one or more electrical lead wires placed within the heart. If an arrhythmia is sensed, the ICD may send a pulse via the electrical lead wires to shock the heart and restore its normal rhythm. Owing to the inherent surgical risks in attaching and replacing electrical leads directly within or on the heart, subcutaneous ICD systems have been devised to provide shocks to the heart without placing electrical lead wires within the heart or attaching electrical wires directly to the heart.

Electrical leads being utilized in subcutaneous systems typically include a single dedicated defibrillation electrode and one or more dedicated pacing and/or sensing electrodes along the length of the lead. Each of these electrodes is electrically connected to separate conductors within the lead body and connected to the ICD. Thus, the capability of the electrical lead to deliver a defibrillation shock, a pacing pulse, or to sense a cardiac depolarization is fixed to the particular longitudinal or radial placement of each electrode.

SUMMARY

The present application advantageously provides an implantable medical electrical lead. The medical electrical lead includes an elongate lead body having a proximal end and a distal portion. A defibrillation electrode positioned along the distal portion of the lead body is included, the defibrillation electrode including a plurality of electrode segments spaced a distance apart from each other. At least one of the plurality of defibrillation electrode segments including at least one coated portion and at least one uncoated portion. The at least one coated portion being coated with an electrically insulating material configured to prevent transmission of a pacing pulse to a patient's heart and configured to allow transmission of a defibrillation shock to the heart. The at least one uncoated portion being configured to transmit a defibrillation shock and at least one of transmit a pacing pulse to the heart and sense a cardiac depolarization. An electrical conductor disposed within the elongate lead body is included, each of the plurality of defibrillation electrode segments being electrically coupled to the electrical conductor.

In another embodiment, the implantable medical lead includes an elongate lead body having a proximal end and a distal portion. A defibrillation electrode positioned along the distal portion of the lead body is included, the defibrillation electrode includes a plurality of electrode segments spaced a distance apart from each other. At least a portion of each of the plurality of defibrillation electrode segments being configured to deliver a defibrillation shock and at least one of deliver a pacing pulse to the heart and sense a cardiac depolarization pulse from a common location on each of the plurality of defibrillation electrode segments. An electrical conductor disposed within the elongate lead body is included, each of the plurality of defibrillation electrodes being electrically coupled to the electrical conductor.

In yet another embodiment, the implantable electrical lead includes an elongate lead body having a proximal end and a distal portion. An electrical conductor is disposed within the elongate lead body. A first defibrillation coil segment and a second defibrillation coil segment are each positioned along the distal portion. The first defibrillation coil segment and the second defibrillation coil segment are spaced a distance apart from each other and are electrically coupled to the electrical conductor. The first defibrillation coil segment and the second defibrillation coil segment have the same polarity when a voltage is applied to the electrical conductor. The first defibrillation coil segment and the second defibrillation coil segment each include at least one coated section being coated with tantalum pentoxide and at least one uncoated section not coated with tantalum pentoxide. The at least one uncoated section being configured to deliver a defibrillation shock and at least one deliver a pacing pulse to the heart and sense a cardiac depolarization. The at least one uncoated section is positioned above the right ventricle when the distal portion of the elongate lead is one of subcutaneously and substernally positioned between a first position proximate the xiphoid process and a second position superior to the xiphoid process.

In a further embodiment, a method for implanting a medical electrical lead is provided. The medical electrical lead includes an elongate lead body having a proximal end and a distal portion of a defibrillation electrode positioned along the distal portion of the lead body, the defibrillation electrode including a plurality of electrode segments spaced a distance apart from each other, at least one of the plurality of defibrillation electrode segments including at least one coated portion and at least one uncoated portion, the at least one coated portion being coated with an electrically insulating material configured to prevent transmission of a pacing pulse to a patient's heart and configured to allow transmission of a defibrillation shock to the heart, the at least one uncoated portion being configured to transmit a defibrillation shock and at least one of transmit a pacing pulse to the heart and sense a cardiac depolarization. The lead may further include an electrical conductor disposed within the elongate lead body, each of the plurality of defibrillation electrode segments being electrically coupled to the electrical conductor. In other examples, the lead may include a connector at a proximal end of the lead, a first electrical conductor disposed within the elongate lead body, the first conductor having a distal end coupled to the first defibrillation electrode segment and a proximal end coupled to the connector, and a second electrical conductor disposed within the elongate lead body, the second conductor having a distal end coupled to the second defibrillation electrode segment and a proximal end coupled to the connector. The method comprises creating an incision at a first location proximate a center of a torso of the patient, introducing an implant tool into the patient through the incision at the first location, advancing a distal end of the implant tool through a substernal space underneath the sternum to create a substernal tunnel, and introducing the medical electrical lead into the substernal tunnel such that the distal portion of the elongate lead body is positioned between a first position proximate the xiphoid process and a second position superior to the xiphoid process such that at least one of the plurality of the defibrillation electrode segments is positioned anterior to and substantially over a ventricle of the heart.

In another embodiment, an implantable medical electrical lead includes an elongate lead body having a proximal end and a distal portion, a defibrillation electrode positioned along the distal portion of the lead body, the defibrillation electrode including a plurality of electrode segments spaced a distance apart from each other, the distance being less than approximately five centimeters, at least one of the plurality of defibrillation electrode segments including at least one coated portion and at least one uncoated portion, the at least one coated portion being coated with an electrically insulating material configured to prevent transmission of a pacing pulse to a patient's heart and configured to allow transmission of a defibrillation shock to the heart, the at least one uncoated portion being configured to transmit a defibrillation shock and at least one of transmit a pacing pulse to the heart and sense a cardiac depolarization.

In another embodiment, an extravascular implantable cardioverter-defibrillator (ICD) system includes an extravascular implantable medical electrical lead and an ICD coupled to the extravascular lead. The extravascular implantable medical electrical lead includes a plurality of defibrillation electrode segments, the plurality of defibrillation electrode segments including a first defibrillation electrode segment and a second defibrillation electrode segment, the second defibrillation electrode segment positioned distal to the first defibrillation electrode segment. The lead further includes a connector at a proximal end of the lead, a first electrical conductor disposed within the elongate lead body, the first conductor having a distal end coupled to the first defibrillation electrode segment and a proximal end coupled to the connector, and a second electrical conductor disposed within the elongate lead body, the second conductor having a distal end coupled to the second defibrillation electrode segment and a proximal end coupled to the connector. The ICD includes a therapy module configured to generate and deliver electrical stimulation therapy and a switch module configured to selectively couple the therapy module to an electrode vector in which both the first and second defibrillation electrode segments simultaneously function as a cathode or anode for delivery of electrical stimulation therapy, e.g., cardioversion/defibrillation therapy or pacing therapy. The switch may also couple the therapy module to each of the first and second electrode segments independently to form an electrode vector that includes only one of the defibrillation electrode segments as an anode or cathode.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

BRIEF DESCRIPTION OF DRAWINGS

A more complete understanding of the present application, and the attendant advantages and features thereof, will be more readily understood by reference to the following detailed description when considered in conjunction with the accompanying drawings wherein:

FIG. 4 is a front view of another embodiment of an extravascular medical electrical lead constructed in accordance with the principles of the present application;

FIG. 5 is a front view of another embodiment of an extravascular medical electrical lead constructed in accordance with the principles of the present application;

FIG. 6 is a front view of another embodiment of an extravascular medical electrical lead constructed in accordance with the principles of the present application; and FIG. 7 is a front view of another embodiment of an extravascular medical electrical lead constructed in accordance with the principles of the present application.

DETAILED DESCRIPTION

Figure 1:
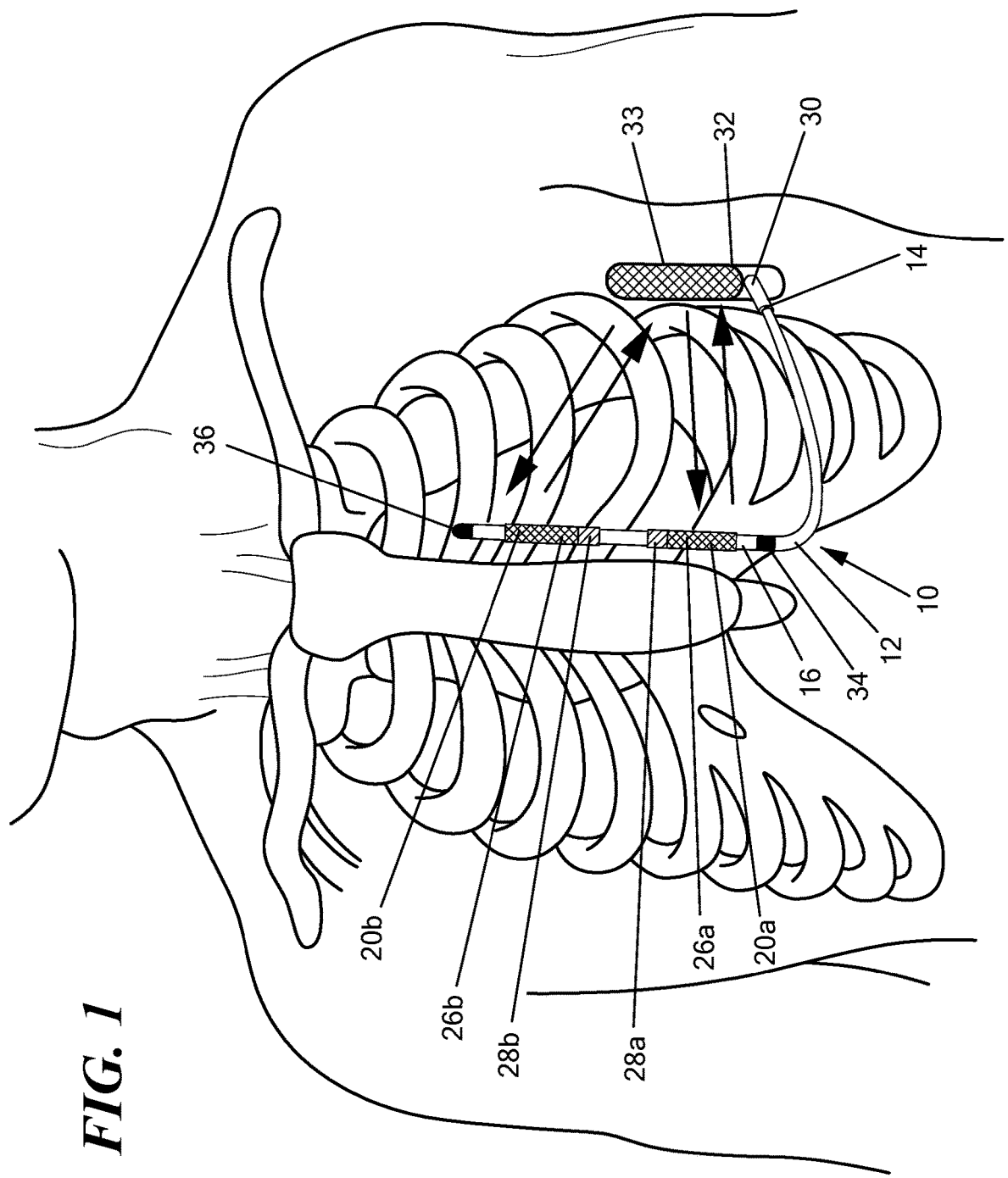
FIG. 1 is a front view of an extravascular medical electrical lead implanted subcutaneously proximate the heart and constructed in accordance with the principles of the present application.

As used here, relational terms, such as "first" and "second," "over" and "under," and the like, may be used solely to distinguish one entity or element from another entity or element without necessarily requiring or implying any physical or logical relationship or order between such entities or elements.

This disclosure describes implantable medical electrical leads, implantable systems utilizing such leads, techniques for providing electrical stimulation therapy using such leads, and methods of the implanting such leads. An example implantable medical electrical lead includes an elongate lead body having a proximal end and a distal portion. The lead includes a defibrillation electrode positioned along the distal portion of the lead body. The defibrillation electrode includes at least two electrode segments made from a conductive material and spaced a distance apart from each other. Between the defibrillation electrode segments is an insulated portion, which may in some instances, be a portion of the leady body. In some instances, the two defibrillation electrode segments function as a common anode or cathode when utilized for delivering therapy and/or sensing electrical signals of the heart. For example, the two or more defibrillation electrode segments are electrically coupled to a common electrical conductor within the lead body. In other instances, the two or more defibrillation electrode segments may be coupled to separate electrical conductors within the lead body. In this case, each of the defibrillation electrode segments may be independently utilized. Additionally, the ICD may include components capable of coupling both of the electrical conductors to therapy circuitry and/or sensing circuitry such that the two or more defibrillation electrode segments may be activated simultaneously by the ICD. For example, the ICD may include a switch module, which may include a switch array, switch matrix, multiplexer, or any other type of switching device suitable to selectively couple defibrillation electrode segments (independently or concurrently) to the therapy circuitry and/or sensing circuitry.

At least one of the defibrillation electrode segments includes at least one coated portion and at least one uncoated portion. The at least one coated portion is coated with an electrically insulating material (such as tantalum pentoxide) capable of blocking or substantially attenuating transmission of signals below a certain voltage level, such as the voltage associated with delivery of pacing pulses (e.g., less than 40 volts), while allowing transmission of signals above a certain voltage level, such as those associated with a high voltage defibrillation or cardioversion shock (e.g., greater than 600 volts). The electrically insulating material may extend around the entire circumference of the at least one coated portion of the defibrillation electrode segment(s). The at least one uncoated portion of the defibrillation electrode segment, on the other hand, allows transmission of low voltage signals as well as high voltage signals. As such, the uncoated portion of the defibrillation electrode segment can be utilized for low voltage applications, such as transmitting a pacing pulse to the heart and/or sensing cardiac activity of the heart. In this manner, the entire electrode surface is used to transmit high voltage stimulation pulses while only the uncoated portion(s) of the defibrillation electrode surface is used to transmit pacing pulses and/or sense electrical signals of the heart.

In one example, only one of the defibrillation electrode segments includes coated and uncoated portions. The other defibrillation electrode segment(s) may be entirely coated. In another example, both of the electrode segments include one or more coated and uncoated portions. Several different lead configurations are described herein having various arrangements of coated and uncoated portions along the length of the defibrillation electrode segments.

In some instances, the defibrillation electrode may be the only electrode such that it provides stimulation and senses electrical signals of the heart. Alternatively, one or more discrete electrodes may be placed along the distal portion of the lead to provide additional pacing and/or sensing functionality. As will be described in further detail here, the discrete electrode(s) may be disposed at various locations along the distal portion of the lead, including distal the defibrillation electrode segments, between two of the defibrillation electrode segments, proximal the defibrillation electrode segments, or various combinations thereof. The discrete electrodes are coupled to electrical conductors within the lead body separate from the electrical conductor(s) coupled to the defibrillation electrode segments.

Figure 2:
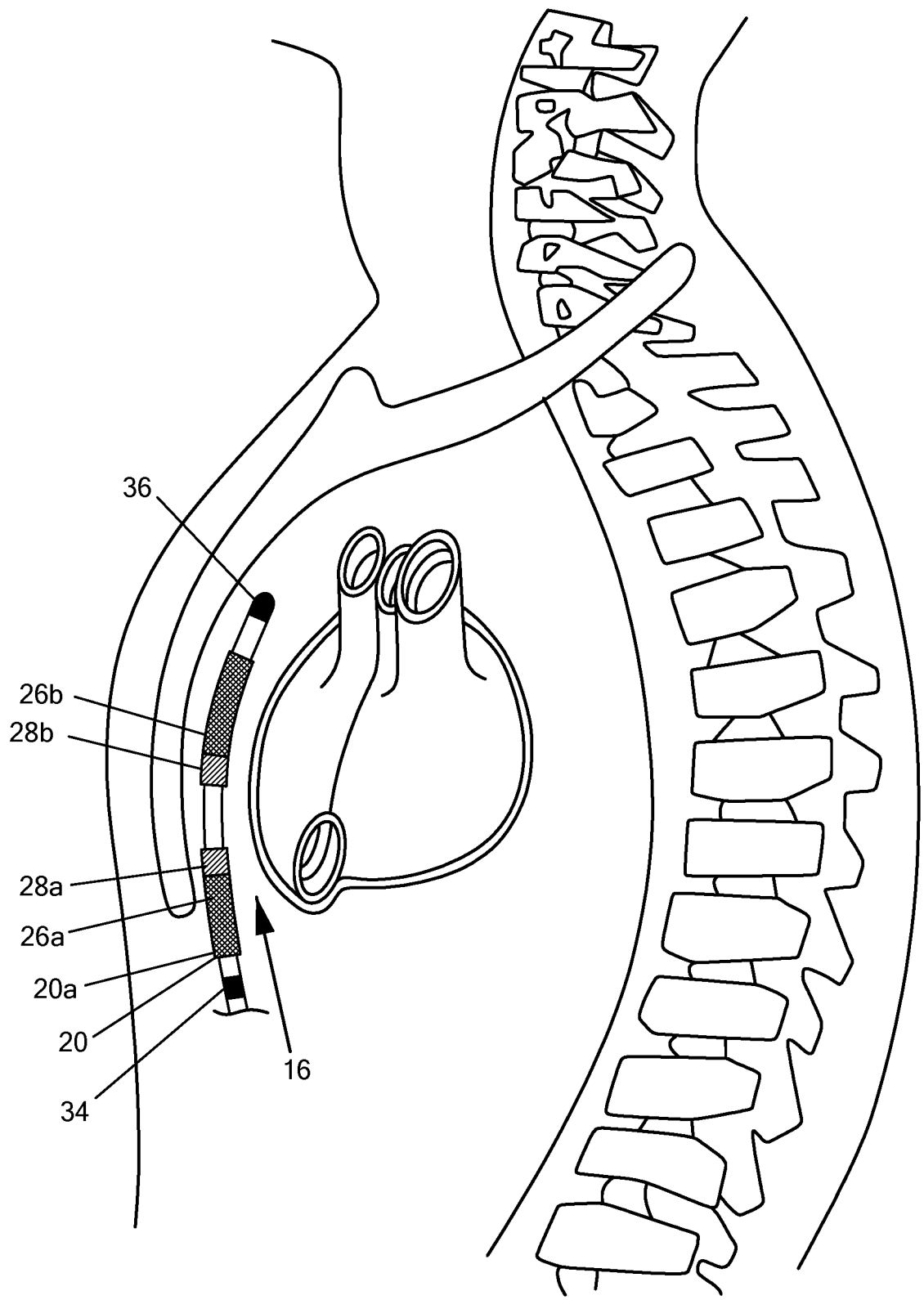
FIG. 2 is a side view of the extravascular medical electrical lead shown in FIG. 1 implanted substernally proximate the heart.
Figure 3:
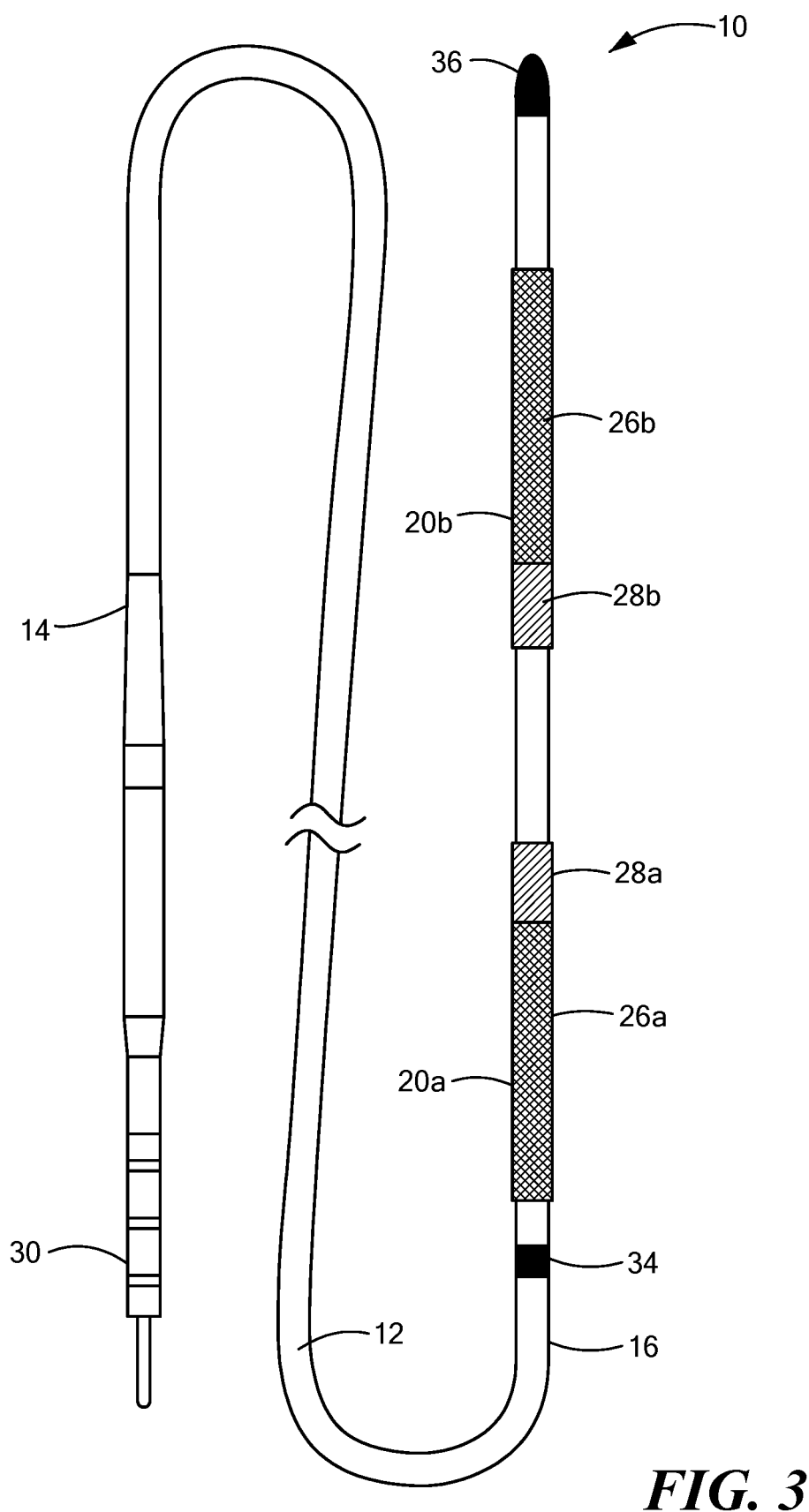
FIG. 3 is a front view of the extravascular medical electrical lead shown in FIG. 1.

Referring now to the drawings in which like reference designators refer to like elements, there is shown in FIGS. 1-3 an exemplary extravascular and/or extracardiac medical system constructed in accordance with the principles of the present application The extravascular and/or extracardiac medical system includes an implantable cardioverter-defibrillator (ICD) 32 coupled to an electrical stimulation lead designated generally as "10." The lead 10 may include an elongate lead body 12 sized to be implanted subcutaneously (FIG. 1) or substernally (FIG. 2) proximate the heart. For example, the lead 10 may extend subcutaneously toward the center of the torso of a patient, for example, toward the xiphoid process of the patient. At a position proximate xiphoid process, the lead body 12 may bend or otherwise turn and extend superiorly, either subcutaneously above the ribcage, or substernally underneath the sternum, in a direction substantially parallel to sternum. Although illustrated in FIG. 1 as being offset laterally from and extending substantially parallel to sternum, the lead 10 may be implanted at other locations, such as over the sternum, under the sternum (as shown in FIG. 2), offset to the right of sternum, angled lateral from the proximal or distal end of the sternum, or the like. Alternatively, lead 16 may be placed along other subcutaneous paths. The path of lead 16 may depend on the location of ICD 14 or other factors.

In one example, the distal portion of lead 10 may be implanted within the anterior mediastinum. The anterior mediastinum may be viewed as being bounded laterally by the pleurae, posteriorly by the pericardium, and anteriorly by the sternum. In some instances, the anterior wall of the anterior mediastinum may also be formed by the transversus thoracis and one or more costal cartilages. The anterior mediastinum includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 10 may be implanted substantially within the loose connective tissue and/or substernal musculature of the anterior mediastinum.

In other embodiments, the distal portion of lead 10 may be implanted in other non-vascular, extra-cardiac, or extra-pericardial locations, including the gap, tissue, or other anatomical features around the perimeter of and adjacent to, but not inserted into, the pericardium or other portion of the heart and not above the sternum or ribcage. As such, lead 10 may be implanted anywhere within the "substernal space" defined by the undersurface between the sternum and/or ribcage and the body cavity but not including the pericardium or other portion of the heart. The substernal space may alternatively be referred to by the terms "retrosternal space" or "mediastinum" or "infrasternal" as is known to those skilled in the art and includes the anterior mediastinum. The substernal space may also include the anatomical region described in Baudoin, Y. P., et al., entitled "The superior epigastric artery does not pass through Larrey's space (trigonum sternocostale)," Surg.Radiol.Anat. 25.3-4 (2003): 259-62. In other words, the distal portion of lead 10 may be implanted in the region around the outer surface of the heart, but not attached to the heart. Moreover, in some instances, substernal space may include inside the pleural membrane.

The lead body 12 may have a generally uniform shape along the length of the lead body 12. In one example, the lead body 12 may have a generally tubular or cylindrical shape and may define a diameter of approximately 3-9 French (Fr), however, lead bodies 12 of less than 3 Fr and more than 9 Fr may also be utilized. In another configuration, the lead body 12 may have a flat, ribbon, or paddle shape along at least a portion of the length of the lead body 12. In such an example, the width across the lead body 12 may be between 1 and 3.5 mm. Other lead body 12 designs may be used without departing from the scope of this application. The lead body 12 of lead 10 may be formed from a non-conductive material, including silicone, polyurethane, fluoropolymers, mixtures thereof, and other appropriate materials, and shaped to form one or more lumens (not shown), however, the techniques are not limited to such constructions.

The lead body 12 may include a proximal end 14 and a distal portion 16 which includes one or more electrodes configured to deliver electrical energy to the heart or sense electrical energy within the heart. The distal portion 16 may be anchored to a desired position within the patient, for example, substernally or subcutaneously by, for example, suturing the distal portion 16 to the patient's musculature, tissue, or bone at the xiphoid process entry site. Alternatively, the distal portion 16 may be anchored to the patient or through the use of rigid tines, prongs, barbs, clips, screws, and/or other projecting elements or flanges, disks, pliant tines, flaps, porous structures such as a mesh-like element that facilitate tissue growth for engagement, bio-adhesive surfaces, and/or any other non-piercing elements. For example, the distal portion 16 may be anchored proximate the xiphoid process or proximate the higher sternal area.

The distal portion 16 may include a defibrillation electrode 18. The defibrillation electrode 18 includes a plurality of defibrillation electrode segments disposed along at least a portion of its length. The plurality of defibrillation electrode segments 20 may be positioned toward the portion of lead body 12 extending, for example, superiorly from the xiphoid process. In the example illustrated in FIGS. 1-3, the defibrillation electrode 18 includes a first defibrillation electrode segment 20a and a second defibrillation electrode segment 20b positioned distal to and spaced a distance apart from the first defibrillation electrode segment 20a. Between the first defibrillation electrode segment 20a and the second defibrillation electrode segment 20b is an insulated portion, which may in some instances, be a portion of the leady body 12. While two defibrillation electrode segments are shown in FIGS. 1-3, it is contemplated that more than two of the plurality of defibrillation electrode segments 20 may be positioned along the distal portion 16. In one configuration, each of the plurality of defibrillation electrode segments 20 may be coil electrodes formed by a conductor. Electrode segments 20 may be formed from any of a number of conductive material(s), including but not limited to, metals, metal oxides, metal alloys, coated metals and composite materials based on a combination of platinum, gold, iridium, titanium, tantalum, vanadium, aluminum, copper, zirconium, carbon, graphene, diamond, zirconium, diamond like coatings (DLC), silicon, and/or boron. This also includes glasses and dielectric materials such as borosilicate or chalcogenide glass, zirconia, alumina as well as conductive polymers, semiconductors and conductive ceramics in pure form or with additives such as boron, carbon, gold, silver and similar metal particles and/or fibers from micro to nano dimensions. In another configuration, each of the plurality of defibrillation electrode segments 20 may be flat ribbon electrode segments, paddle electrode segments, braided or woven electrode segments, mesh electrode segments, directional electrode segments, patch electrode segments or other types of electrode segments configured to deliver a defibrillation shock to the patient's heart.

In an exemplary configuration, the first defibrillation electrode segment 20a and the second defibrillation electrode segment 20b are coil electrodes disposed in-line with, around the exterior of, or within the wall of the lead body 12. Each of the first defibrillation electrode segment 20a and the second defibrillation electrode segment 20b may be approximately 1-10 cm in length and, more preferably, 2-6 cm in length and, even more preferably, 3-5 cm in length. However, lengths of greater than 10 cm and less than 1 cm may be utilized without departing from the scope of this disclosure. The first defibrillation electrode segment 20a and the second defibrillation electrode segment 20b may be the same length or each segment may have a different length.

In one example, the first defibrillation electrode segment 20a may be spaced apart from the second defibrillation electrode segment 20b by approximately 1 mm-3 cm. In another example, the first defibrillation electrode segment 20a may be spaced apart from the second defibrillation electrode segment 20b by approximately 0.5-2 cm. In a further example, the first defibrillation electrode segment 20a may be spaced apart from the second defibrillation electrode segment 20b by approximately 0.5-1 cm. In another example, first defibrillation electrode segment 20a may be positioned proximal to and spaced apart from the second defibrillation electrode segment 20b by approximately 2-10 mm.

Each of the plurality of defibrillation electrode segments 20a and 20b may include at least one coated portion 26a and 26b, respectively, and at least one uncoated portion 28a and 28b, respectively, at any longitudinal position along each of their respective lengths. In the example illustrated in FIGS. 1-3, uncoated portion 28a is disposed on the distal end of the first defibrillation electrode segment 20a and uncoated portion 28b is disposed on the proximal end of the second defibrillation electrode segment 20b. As will be described in further detail herein, however, the coated portions 26 and uncoated portions 28 may be disposed at other locations along the length of the defibrillation electrode segments 20, e.g., at the proximal end, distal end, or anywhere between. Additionally, one or both defibrillation electrode segments 20a or 20b may include more than one coated portion 26 and/or more than one uncoated portion 28, e.g., an uncoated portion 28 between two coated portions 26 or a coated portion 26 between two uncoated portions 28. In other instances, only one of defibrillation electrode segment 20a or 20b may include coated portion(s) 26 and/or uncoated portion(s) 28 while the other of the defibrillation electrode segments 20 is entirely coated or uncoated.

Each of the coated portions 26 of the plurality of defibrillation electrode segments 20 may be coated with an electrically insulating material that substantially prevents, blocks, or attenuates the transmission or delivery of low voltage signals (e.g., signals having voltages less than 100 volts) while not substantially preventing, blocking or attenuating the transmission or delivery of high voltage signals (e.g., signals having voltages greater than 500 volts). In this manner, the entirety of each of the plurality of defibrillation electrode segments 20 (i.e., uncoated portion(s) 28 in conjunction with the coated portion(s) 26) is configured to deliver a high voltage therapy, such as a defibrillation or cardioversion shock, and each of the uncoated portion(s) 28 of each of the plurality of electrode segments 20 is configured to deliver low voltage therapies, such as one or more pacing pulses of varying voltages for anti-tachycardia pacing, post-shock pacing, bradycardia pacing, high rate pacing for VF induction, and/or entrainment pacing pulses before T-shock for VF induction and/or to sense low voltage signals, such as cardiac depolarizations.

The electrically insulating material may extend around the entire circumference of the coated portion(s) 26 of the defibrillation electrode segment(s) 28. The electrically insulating material may be any of a number of materials, such as single or combinations of tantalum pentoxide, titanium oxides, zirconium oxide, vanadium oxide, niobium oxide, doped silicon, silicon dioxide, boron doped diamond, doped glass, ceramic coating or polymer composite or other material that has the property of substantially preventing the transmission or delivery of low voltages while not substantially preventing the transmission or delivery of high voltages. The thickness of the insulating material may have a thickness that varies based on the type of material of electrode segment 20, the type of insulating material, the dimensions of the coated portion 26, the expected depth and position of the distal portion 16, e.g., substernal or subcutaneous location, and the like. For tantalum pentoxide, for example, the thickness of the coating may range from approximately greater than or equal to 0.2 to less than or equal to 2.0 microns. However, other thicknesses may be utilized without departing from the scope of this disclosure. In one example, the coated portions 26 are coated with tantalum pentoxide with a thickness of 0.6 to 0.9 microns that significantly blocks current flow up to 90V of electrical pulses toward the patient's heart and prevents the sensing of a cardiac depolarization event to determine if electrical stimulation therapy should be delivered to the heart. However, at higher voltages, for example at voltages higher than 90V, the voltage overcomes the electrically insulating property of the tantalum pentoxide and a defibrillation shock may be delivered to heart.

The coated portions 26 and uncoated portions 28 may vary in size. In some configurations, uncoated portions 28 may be less than or equal to 25% of the length the respective electrode segment 20. In another exemplary configuration, uncoated portions 28 may be less than or equal to 10% of the length of the respective electrode segment 20. In other instances, each of the uncoated portions 28 may have a surface area that is less than or equal to 25% of the total surface area of the respective defibrillation electrode segment 20 or less than or equal to 10% of the total surface area of the respective defibrillation electrode segment 20. In still further examples, the combined length and or surface area of all of the uncoated portions 28 of segments 20 may be less than or equal to 25% of the total length or surface area of the plurality of segments 20 or less than or equal to 10% of the total length or surface area of the plurality of segments 20. Alternatively, each of the uncoated portions 28 may, in some examples, have a surface area that is less than or equal to 100 square millimeters (mm$^2$). In other instances, uncoated portions 28 may have a surface area that is less than or equal to 10 mm$^2$. Uncoated and coated portions may have sizes other than those described above.

Various arrangements of each uncoated portion 28 and each coated portion 26 are contemplated and are discussed in more detail below. In a particular embodiment, one or more of the uncoated portions 28 of the first defibrillation electrode segment 20a and/or the second defibrillation electrode segment 20b may be positioned over any desired chamber or region of the patient's heart. For example, the distal portion 16 of the lead body 12 may be positioned over the cardiac silhouette, as seen under anterior-posterior fluoroscopy, such that both the uncoated portion 28a of the first defibrillation electrode segment 20a and the second defibrillation electrode segment 20b are positioned substantially over a ventricle or other cardiac target. In one instance, the distal portion 16 of the lead body 12 may be positioned over the cardiac silhouette, as seen under anterior-posterior fluoroscopy, such that the insulated portion between the defibrillation electrode segments 20 is substantially centered over a ventricle or other cardiac target. As described in detail herein, uncoated portions 28 are used both to deliver a pacing pulse and/or sense a cardiac depolarization (low voltage functions) and to deliver a high voltage defibrillation or cardioversion shock (high voltage functions). The plurality of defibrillation electrode segments 20 may also be positioned over the right ventricle or any other location above the heart or along the lead body but not directly above the heart such that multiple therapy vectors can be created along the length of the distal portion 16, as discussed in more detail below.

The lead body 12 may also include one or more discrete electrodes 34 and/or 36 located along the distal portion 16. In the examples illustrated in FIGS. 1-3, electrode 34 is located proximal to the first defibrillation electrode segment 20a and electrode 36 is located distal the second defibrillation electrode segment 20b. Electrodes 34 and 36 are spaced apart from respective defibrillation electrode segments 20 by a distance. In one example, electrodes 34 and 36 are spaced apart from respective defibrillation electrode segments 20 by greater than or equal to 2 mm and less than or equal to 1.5 cm. In another example, electrodes 34 and 36 are spaced apart from respective defibrillation electrode segments 20 by greater than or equal to 5 mm and less than or equal to 1 cm. In a further example, electrodes 34 and 36 are spaced apart from respective defibrillation electrode segments 20 by greater than or equal to 6 mm and less than or equal to 8 mm. However, electrodes 34 and 36 may be spaced apart from respective defibrillation electrode segments by a distance greater than 1.5 cm in other configurations, particularly when the discrete electrode is located proximal to all defibrillation electrode segments 20 and distal to all defibrillation electrode segments 20.

Electrode 34 is shown as a ring electrode and electrode 36 is shown as a hemispherical tip electrode. However, electrodes 34 and 36 may comprise any of a number of different types of electrodes, including ring electrodes, short coil electrodes, paddle electrodes, hemispherical electrodes, directional electrodes, or the like, and may be positioned at any position along the distal portion 16. Further, electrodes 34 and 36 may be of similar type, shape, size and material or may differ from each other. In another embodiment, for example, electrode 36 may not be a tip electrode but instead may be located proximal to the distal end of the lead body 12 and distal the second defibrillation electrode segment 20b. The discrete electrodes 34 and 36 may be low-voltage electrodes configured to deliver pacing pulses to the heart and/or sense cardiac depolarizations of the heart. Each electrode 34 and 36 may be coupled to its own conductor, for example one or more wires disposed within separate lumens of the lead body 12, such that each electrode 34 and 36 may be independently activated by the ICD 32. In other embodiments, lead body 12 may include a single discrete electrode (e.g., electrode 34 or 36) or more than two discrete electrodes located along the distal portion 16. In another embodiment, lead body 12 may not include any discrete electrodes along the distal portion 16 of lead body 12. In this case, the defibrillation electrode segments 20 are the sole electrodes of lead 10 used for low voltage functionality (e.g., sensing or pacing) and for high voltage electrical stimulation therapy.

In some instances, the distal portion of lead body 12 from the distal end of lead body 12 to the proximal side of the most proximal electrode (e.g., electrode 34 in the example of FIG. 1) may be less than or equal 15 cm and, more preferably, less than or equal to 13 cm and even more preferably less than or equal to 10 cm.

The proximal end 14 of the lead body 12 may include one or more connectors 30 (best seen in FIG. 3) to electrically couple the lead 10 to an implantable cardioverter-defibrillator (ICD) 32 subcutaneously or submuscularly implanted within the patient, for example, under the left armpit of the patient. The ICD 32 may include a housing 33 that forms a hermetic seal that protects components of ICD 32. The housing 33 of ICD 32 may be formed of a conductive material, such as titanium or titanium alloy, which may function as a housing electrode for a particular therapy vector as illustrated by the arrows in FIG. 1 between the housing 33 and the distal portion 16. The ICD 32 may also include a connector assembly that includes electrical feedthroughs through which electrical connections are made between the one or more connectors 30 of lead 10 and electronic components included within the housing 33. The housing 33 may house one or more processors, memories, transmitters, receivers, sensors, sensing circuitry, therapy circuitry (which may include, for example, a pulse generator(s), transformer(s), capacitor(s), or the like), switching module, power sources (capacitors and batteries) and other appropriate components.

As described above, the defibrillation electrode segments 20 may function as a common electrical pole. In such a configuration, both the first defibrillation electrode segment 20a and the second defibrillation electrode segment 20b may be simultaneously used as an anode or cathode of an electrode vector used to provide electrical stimulation therapy to the patient and/or sense the electrical signals of the heart of the patient. In other words, when the electrical conductor coupled to the first defibrillation electrode segment 20a and the second defibrillation electrode segment 20b is electrically coupled to a therapy circuit and/or sensing circuit inside ICD 32, the uncoated portions function as a single anode/cathode for pacing and/or sensing applications. For example, a single wire conductor (not shown) may be disposed within a lumen of the lead body 12 that is electrically coupled to the connector 30. The single conductor may branch off in the lead body 12 at a predetermined longitudinal position into two or more wire conductors to connect to each of the plurality of electrode segments 20. Alternatively, a first conductor may connect to the first defibrillation electrode segment 20a and a second conductor may connect the first defibrillation electrode segment 20a to the second defibrillation electrode segment 20b, such that application of a voltage to the first conductor applies the same voltage to the first defibrillation electrode segment 20a and the second defibrillation electrode segment 20b.

In other configurations, the first defibrillation electrode segment 20a and the second defibrillation electrode segment 20b are coupled to separate conductors within the lead body 12. For example, a first electrical conductor disposed within the elongate lead body 12 may have a distal end coupled to the first defibrillation electrode segment 20a and a proximal end coupled to the connector 30 and a second electrical conductor disposed within the elongate lead body 12 has a distal end coupled to the second defibrillation electrode segment 20b and a proximal end coupled to the connector 30. In this case, each of the defibrillation electrode segments 20 may be independently utilized as part of an electrode vector. Additionally, ICD 32 may include components capable of coupling both of the electrical conductors simultaneously to therapy circuitry such that both of the defibrillation electrode segments may be activated simultaneously by the ICD 32. For example, ICD 32 may include switching circuitry or switch module to select which of the available electrodes are used to deliver the electrical stimulation therapy. The switch module may include a switch array, switch matrix, multiplexer, or any other type of switching device suitable to selectively couple electrodes to the therapy circuitry. ICD 32 may therefore use the switch module to select the electrodes 20a, 20b, 33, 34, and/or 36 to function as the electrode vector for delivery the therapy. In instances in which defibrillation electrode segments 20a and 20b are coupled to separate conductors, ICD 32 may selectively couple the therapy circuitry (or sensing circuitry) to either one of segments 20a and 20b individually as an anode or cathode of the electrode vector or to both of the electrode segments 20A and 20B concurrently as a cathode or anode of the electrode vector. Likewise other ones of electrodes 34 and 36 and/or housing electrode 33 may be selected for use as part of an electrode vector (including any of the various electrode vectors described herein) via the switch module.

The ICD 32 may generate and deliver electrical stimulation therapy, including traditional low voltage stimulation therapies (e.g., anti-tachycardia pacing, post-shock pacing, bradycardia pacing, or pacing used in conjunction with VF induction) as well as traditional high voltage stimulation therapies (e.g., cardioversion or defibrillation shocks) via various electrode combinations or vectors. In one example, ICD 32 may be configured to deliver low voltage stimulation therapy via an electrode vector that includes the uncoated portions 28 of electrode segments 20 as an anode (or cathode) and the housing of the ICD 32 as the cathode (or anode). In some instances, this same vector may be utilized for sensing electrical signals of the heart. Likewise, ICD 32 may be configured to deliver high voltage stimulation therapy via the electrode vector that includes electrode segments 20 (both the uncoated portions 28 and coated portions 26) as an anode (or cathode) and the housing of the ICD 32 as the cathode (or anode). In other instances, the uncoated portions 28a and/or 28b may also be utilized individually, such that the low voltage stimulation therapy may be provided between uncoated portions 28a and uncoated portion 28b or between either one of uncoated portions 28a or 28b and another one of the electrodes (e.g., electrode 34, electrode 36, and/or housing electrode 33).

ICD 32 may deliver low voltage electrical energy, e.g., pacing pulses, using any of a variety of electrode vectors that include the uncoated portions 28a and 28b (individually or collectively) of defibrillation electrode segments 20, and/or electrode 34, and/or electrode 36, and/or housing electrode 33. For example, ICD 32 may deliver pacing pulses via an electrode vector in which one of electrode 34, electrode 36, or the uncoated portions 28a and 28b (individually or collectively) is a cathode and the housing electrode 33 is an anode or vice versa. In another example, ICD 32 may deliver pacing pulses via an electrode vector formed from various pairs or multiple configurations of electrode 34, electrode 36 and the uncoated portions of 28a and 28b (individually or collectively), e.g., one or more of the electrodes serve as a cathode and another one or more of the electrodes serve as an anode. In yet another example, ICD 32 may deliver pacing pulses via an electrode vector between any combination of electrode 34, electrode 36 and uncoated portions 28 (individually or collectively) concurrently used as a cathode and the housing electrode 33 as an anode or vice versa, as is the case in multi-site or multi-point pacing.

In one example, ICD 32 may detect a ventricular tachyarrhythmia (e.g., VT or VF) based on signals sensed using one of the electrode vectors described herein with respect to FIGS. 1-10 and using any tachyarrhythmia detection algorithm know in the art. In response to detecting the tachyarrhythmia, ICD 32 generates low voltage and/or high voltage electrical stimulation therapy and delivers the electrical stimulation therapy via one of the electrode vectors described herein with respect to FIGS. 1-10. ICD 32 may, in some instances, generate and deliver the low energy stimulation therapy via any of the electrode vectors described above and generate and deliver the high energy stimulation therapy via one or both defibrillation electrode segments 20 (individually or concurrently).

In one example, ICD 32 may deliver pacing (e.g., ATP or post-shock pacing) using an electrode vector that includes one or both defibrillation electrode segments 20a and/or 20b. The electrode vector used for pacing may, for example, include electrode segment 20a as a cathode (or anode) and one of electrode segment 20b and/or electrodes 33, 34, or 36 as the anode (or cathode) or include segment 20b as a cathode (or anode) and one of electrode segment 20a and/or electrodes 33, 34, or 36 as the anode (or cathode), or include segments 20a and 20b together as a common cathode (or anode) and one electrodes 33, 34, or 36 as the anode (or cathode). If high voltage therapy is necessary, ICD 14 may deliver a cardioversion/defibrillation shock (or multiple shocks) using both of electrode segments 20a or 20b concurrently as the cathode and housing electrode 33 as the anode.

ICD 32 may also generate and deliver electrical stimulation signals for inducing VF, e.g., high rate pacing pulses and/or entrainment pacing pulses preceding a T-shock. In one example, ICD 32 may deliver high rate pacing pulses using an electrode vector between uncoated portion 28a on defibrillation electrode segment 20a and uncoated portion 28b of defibrillation electrode segment 20b. In another example, ICD 32 may deliver a plurality of entrainment pacing pulses (e.g., 3-5 pulses) using an electrode vector between uncoated portion 28a on defibrillation electrode segment 20a and uncoated portion 28b of defibrillation electrode segment 20b and then deliver a T-wave shock via one or both of defibrillation electrode segments 20a and 20b.

Electrode segments 20A and 20B are referred to as defibrillation electrode segments or defibrillation electrodes because they are utilized, individually or collectively, for delivering high voltage stimulation therapy (e.g., cardioversion or defibrillation shocks). However, electrode segments 20A and 20B may also be utilized to provide pacing functionality, sensing functionality or both pacing and sensing functionality in addition to or instead of high voltage stimulation therapy. In this sense, the use of the terms "defibrillation electrode segments" or "defibrillation electrode" should not be considered as limiting the electrode segments to use in only high voltage applications.

FIG. 4 illustrates another configuration of a distal portion 40 of another example lead body 42. The lead body 42 can include one or more of the structure and/or functionality of lead body 12 described in detail with respect to FIGS. 1-3 (and vice versa), including the dimensions, materials, and the like. Repetitive description of like numbered elements described in other embodiments is omitted for sake of brevity.

In the example shown in FIG. 4, the first defibrillation electrode 20a is positioned proximal to and spaced apart from the second defibrillation electrode 20b. In one example, the first defibrillation electrode segment 20a may be spaced apart from the second defibrillation electrode segment 20b by approximately 1 mm-3 cm. In another example, the first defibrillation electrode segment 20a may be spaced apart from the second defibrillation electrode segment 20b by approximately 1-2 cm. In a further example, the first defibrillation electrode segment 20a may be spaced apart from the second defibrillation electrode segment 20b by approximately 1.5 cm. In another example, the first defibrillation electrode segment 20a may be spaced apart from the second defibrillation electrode segment 20b by approximately 1-3 cm. In another example, the first defibrillation electrode segment 20a may be spaced apart from the second defibrillation electrode segment 20b by less than approximately 5 cm. In another example, first defibrillation electrode segment 20a may be positioned proximal to and spaced apart from the second defibrillation electrode segment 20b by approximately 2-10 mm. However, other spacing distances between segments 20 may be utilized (such as those described above with respect to FIGS. 1-3) without departing from the scope of this disclosure.

The first defibrillation electrode segment 20a includes one coated portion 26a distal to one uncoated portion 28a along its length. The second defibrillation electrode segment 20b includes one coated portion 26b proximal to one uncoated portion 28b. The uncoated portions 28 and coated portions 26 may have any of the sizes (e.g., surface areas or percentage lengths) described above with respect to FIGS. 1-3.

Spaced between the coated portion 26a of the first defibrillation electrode segment 20a and the coated portion 26b of the second defibrillation electrode segment 20a are discrete electrodes 34a and 34b. Electrodes 34a and 34b may be spaced apart from coated portions 26a and 26b, respectively, by a distance. In one example, the distance between electrode 34a (or 34b) and the respective coated portion 26a (or 26b) may be approximately 2 mm-1 cm. In another example, the distance between electrode 34a (or 34b) and the respective coated portion 26a (or 26b) may be approximately 2 mm-6 mm. In other embodiments, distal portion 40 may include no discrete electrode 34, a single discrete electrode 34 or more than two discrete electrodes 34 located between defibrillation electrode segments 20. In one example, a single short coil electrode (e.g. having a length of approximately 0.5-3 cm) may be located between defibrillation electrode segments 20.

Distal portion 40 further includes a tip electrode 36 that may conform substantially with electrode 36 of distal portion 16. Tip electrode 36 may be located at the distal end of lead body 40 (as shown) or anywhere distal of defibrillation electrode segment 20b. In some instances, distal portion 40 may not include electrode 36. In addition to or instead of the tip electrode 36, distal portion 40 may include at least one discrete electrode located proximal to defibrillation electrode segment 20a. In yet another embodiment, the distal portion 40 may not include any discrete electrodes. Electrodes 34a, 34b, and 36 may be any of the types, shapes, size, and materials of electrodes described above with respect to FIGS. 1-3 and may be the same or different from each other.

In such a configuration, ICD 32 may deliver low voltage electrical energy, e.g., pacing pulses, using any of a variety of electrode vectors that include the uncoated portions 28a and 28b of defibrillation electrode segments 20 (individually or collectively), and/or electrodes 34a, and/or 34b, and/or 36, and/or housing electrode 33. For example, ICD 32 may deliver pacing pulses via an electrode vector in which one of electrode 34*a*, 34*b*, 36, or the uncoated portions 28*a* and 28*b* (individually or collectively) is a cathode and the housing electrode 33 is an anode or vice versa. In another example, ICD 32 may deliver pacing pulses via an electrode vector formed from various pairs or multiple configurations of electrodes 34*a*, 34*b*, 36 and the uncoated portions of 28*a* and 28*b* (individually or collectively), e.g., one or more of the electrodes serves as a cathode and another one or more of the electrodes serves as an anode. In yet another example, ICD 32 may deliver pacing pulses via an electrode vector between any combination of electrodes 34*a*, 34*b*, 36 and uncoated portions 28 (individually or collectively) concurrently used as a cathode and the housing electrode 33 as an anode or vice versa, as is the case in multi-site or multi-point pacing.

FIG. 5 illustrates another configuration of a distal portion 50 and another example lead body 52. The lead body 52 can include one or more of the structure and/or functionality of lead body 12 described in detail with respect to FIGS. 1-4 (and vice versa) and/or lead body 42 of FIG. 4 (and vice versa), including the dimensions, materials, and the like. Repetitive description of like numbered elements described in other embodiments is omitted for sake of brevity.

The first defibrillation electrode segment 20*a* is positioned proximal to and spaced a distance apart from the second defibrillation electrode segment 20*b*. The distance between the defibrillation electrode segments 20 may be any of those described above with respect to FIGS. 1-4. The first defibrillation electrode segment 20*a* includes one uncoated portion 28*a* distal to one coated portion 26*a* along its length. The second defibrillation electrode segment 20*b* includes one uncoated portion 28*b* distal to one coated portion 26*b* along its length. The coated portions 26 and uncoated portions 28 may have any of the sizes (e.g., areas or percentage lengths) described above with respect to FIGS. 1-4.

In the example shown in FIG. 5, a first discrete electrode 34*a* is disposed proximal to the coated portion 26*a* of defibrillation electrode segment 20*a*, a second discrete electrode 34*b* is disposed between the uncoated portion 28*a* of defibrillation electrode segment 20*a* and the coated portion 26*b* of defibrillation electrode segment 20*b*, a third discrete electrode (tip electrode) 36 is disposed distal to the uncoated portion 28*b* of defibrillation electrode segment 20*b*.

Electrodes 34*a*, 34*b*, and 36 are spaced apart from coated defibrillation electrode segments 20. Electrodes located adjacent to any uncoated portions 28 of defibrillation electrode segments 20 (e.g., electrode 34*b* or 36 in FIG. 5) may be spaced apart from the adjacent uncoated portion 28 by greater than or equal to 2 mm and less than or equal to 1.5 cm. In another example, electrodes located adjacent to any uncoated portions 28 of defibrillation electrode segments 20 may be spaced apart from uncoated portions 28 by greater than or equal to 5 mm and less than or equal to 1 cm. In a further example, electrodes located adjacent to any uncoated portions 28 of defibrillation electrode segments 20 may be spaced apart from uncoated portions 28 by greater than or equal to 6 mm and less than or equal to 8 mm.

Electrodes located adjacent to any coated portions 26 of defibrillation electrode segments 20 (e.g., electrode 34*a* or 34*b* in FIG. 5) may be spaced apart from the adjacent coated portion 26 by greater than or equal to 2 mm and less than or equal to 1.5 cm. In another example, electrodes located adjacent to any coated portions 26 of defibrillation electrode segments 20 may be spaced apart from coated portions 26 by greater than or equal to 2 mm and less than or equal to 1 cm. In a further example, electrodes located adjacent to any coated portions 26 of defibrillation electrode segments 20 may be spaced apart from coated portions 26 by greater than or equal to 2 mm and less than or equal to 6 mm. Other electrode spacing may be utilized within departing from the scope of this disclosure.

In other configurations, there may be more or fewer discrete electrodes. For example, distal portion 50 may include only a single electrode 34*b* disposed between the defibrillation electrode segments 20. In another example, distal portion 50 may include the electrode 34*b* disposed between defibrillation electrode segments 20 and only one of discrete electrodes 34*a* and 36. In still other examples, there may be more than one electrode 34*a* located proximal to defibrillation electrode segment 20*a* and/or more than one electrode 34*b* located between the defibrillation electrode segments 20 and/or more than one electrode distal to defibrillation electrode segment 20*b* and/or one or more or all of electrodes 34*a*, 34*b* or 36 may be absent. Further, any of electrodes 34*a*, 34*b* and 36 may be of similar type, shape, size and material or may differ from each other. In another embodiment, for example, electrode 36 may not be a tip electrode but instead may be located proximal to the distal end of the lead body 12 and distal the second defibrillation electrode segment 20*b*.

In such a configuration, ICD 32 may deliver low voltage electrical energy, e.g., pacing pulses, using any of a variety of electrode vectors that include the uncoated portions 28*a* and 28*b* of defibrillation electrode segments 20 (individually or collectively), and/or electrodes 34*a*, and/or 34*b*, and/or 36, and/or housing electrode 33. For example, ICD 32 may deliver pacing pulses via an electrode vector in which one of electrode 34*a*, 34*b*, 36, or the uncoated portions 28*a* and 28*b* (individually or collectively) is a cathode and the housing electrode 33 is an anode or vice versa. In another example, ICD 32 may deliver pacing pulses via an electrode vector formed from various pairs or multiple configurations of electrodes 34*a*, 34*b*, 36 and the uncoated portions of 28*a* and 28*b* (individually or collectively), e.g., one or more of the electrodes serves as a cathode and another one or more of the electrodes serves as an anode. In yet another example, ICD 32 may deliver pacing pulses via an electrode vector between any combination of electrodes 34*a*, 34*b*, 36 and uncoated portions 28 (individually or collectively) concurrently used as a cathode and the housing electrode 33 as an anode or vice versa, as is the case in multi-site or multi-point pacing.

FIG. 6 illustrates another configuration of a distal portion 60 and another lead body 62. Lead body 62 can include one or more of the structure and/or functionality of lead body 12 described in detail with respect to FIGS. 1-3 (and vice versa), lead body 42 described in detail with respect to FIG. 4 (and vice versa), and/or lead body 52 described in detail with respect to FIG. 5 (and vice versa), including the dimensions, materials, and the like. Repetitive description of like numbered elements described in other embodiments is omitted for sake of brevity.

The distal portion 60 of lead body 62 conforms substantially to the distal portion 50 of lead body 52 of FIG. 5, except that the coated portions 26*a* and 26*b* and uncoated portions 28*a* and 28*b* of the defibrillation electrode segments 20*a* and 20*b* are different. In the example shown in FIG. 6, the first defibrillation electrode 20*a* includes one coated portion 26*a* distal to one uncoated portion 28*a* along its length and the second defibrillation electrode segment 20*b* includes one coated portion 26*b* distal to one uncoated portion 28b. The discrete electrodes 34a, 34b, and 36 may be arranged in any of the configurations described above with respect to FIGS. 1-5.

In other configurations, the uncoated portions 28a and 28b or electrodes 34a, 34b, and 36 of lead bodies 12, 42, 52, and 62 may be shaped, oriented, designed or otherwise configured to reduce extra-cardiac stimulation. For example, the uncoated portions 28a and 28b of lead body 12 may be shaped, oriented, designed or otherwise configured to focus, direct, or point pacing pulses to the heart. In this manner, pacing pulses delivered by the uncoated portions 28a and 28b are directed toward the heart and not outward toward skeletal muscle. For example, the coated portion may extend less than or equal to 180 degrees around the circumference of the lead body 12, and in an exemplary configuration, less than or equal to 120 degrees. In an exemplary configuration, as shown in FIG. 7, either or both of the uncoated portions 28a and 28b are disposed in a side-by-side relationship with their respective coated portion 26a and 26b across their respective first defibrillation electrode 20a or second defibrillation electrode 20b. For example, as shown in FIG. 7, at a particular longitudinal position on the lead bodies 12, 42, 52, and 62 uncoated portions 28a and 28b may be partially disposed around the circumference or perimeter of the lead bodies 12, 42, 52, and 62 and the remaining portion of the circumference or perimeter of the lead bodies 12, 42, 52, and 62 may include the insulating material of coated portions 26a and 26b. In other longitudinal positions of coated portions 26a and 26b, the electrically insulating material may extend around the entire circumference of the coated portion(s) 26 of the defibrillation electrode segment(s) 20.

Figure 8:
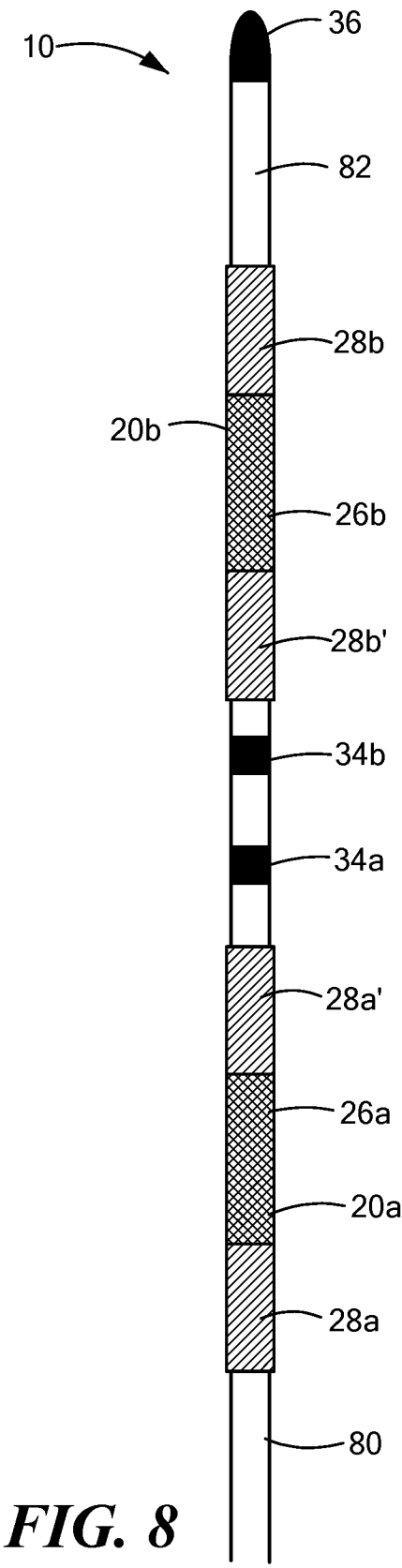
FIG. 8 is a front view of another embodiment of an extravascular medical electrical lead constructed in accordance with the principles of the present application.

FIG. 8 illustrates another configuration of a distal portion 80 and a lead body 82. The lead body 82 can include one or more of the structure and/or functionality of lead body 12 of FIGS. 1-3 (and vice versa), lead body 42 of FIG. 4 (and vice versa), lead body 52 of FIG. 5 (and vice versa), lead body 62 of FIG. 6 (and vice versa), or the lead body of FIG. 7 (and vice versa), including the dimensions, materials, and the like. Repetitive description of like numbered elements described in other embodiments is omitted for sake of brevity.

In the example shown in FIG. 8, the first defibrillation electrode segment 20a is positioned proximal to and spaced apart from the second defibrillation electrode segment 20b. The distance between the defibrillation electrode segments 20 may be any of those described above with respect to FIGS. 1-7. The first defibrillation electrode segment 20a includes one coated portion 26a disposed between a first coated portion 28a and a second coated portion 28a'. The second defibrillation electrode segment 20b also includes one coated portion 26b disposed between a first uncoated portion 28b and a second uncoated portion 28b'. Each of the uncoated portions 28 may have any of the sizes (e.g., surface areas or percentage lengths) described above with respect to FIGS. 1-7. Alternatively, the total size (e.g., surface area or percentage length) of uncoated portions 28a and 28a' may be the sizes described above with respect to FIGS. 1-7. Likewise, the total size (e.g., surface area or percentage length) of uncoated portions 28b and 28b' may be the sizes described above with respect to FIGS. 1-7.

Spaced between the first defibrillation electrode segment 20a and the second defibrillation electrode segment 20b may be discrete electrodes 34a and 34b. Additionally, the distal portion 80 also includes a tip electrode 36. However, the distal portion 80 of lead 82 may include more or fewer discrete electrodes arranged in any of the manners described above with respect to FIGS. 1-7. The discrete electrodes may include the types, spacings, sizes, and/or materials described above with respect to FIGS. 1-7 as well.

Figure 9:
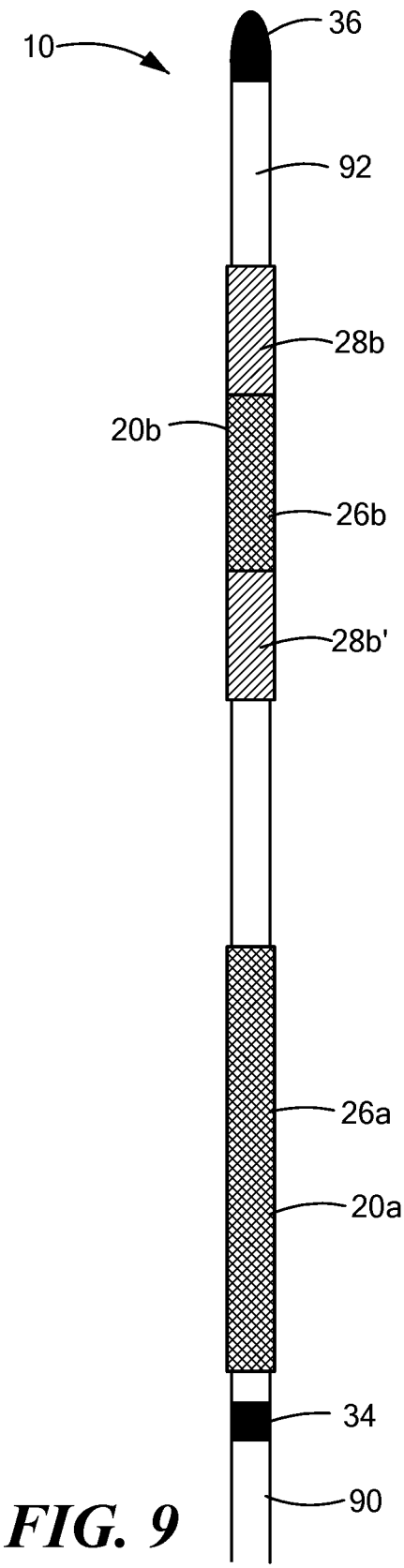
FIG. 9 is a front view of another embodiment of an extravascular medical electrical lead constructed in accordance with the principles of the present application.

FIG. 9 illustrates another configuration of a distal portion 90 and a lead body 92. The lead body 92 can include one or more of the structure and/or functionality of lead body 12 of FIGS. 1-3 (and vice versa), lead body 42 of FIG. 4 (and vice versa), lead body 52 of FIG. 5 (and vice versa), lead body 62 of FIG. 6 (and vice versa), the lead body 72 of FIG. 7 (and vice versa), and/or the lead body 82 of FIG. 8 (and vice versa), including the dimensions, materials, and the like. Repetitive description of like numbered elements described in other embodiments is omitted for sake of brevity.

In the configuration shown in FIG. 9, only one of the defibrillation electrode segments 20 includes an uncoated portion 28. In particular, the second defibrillation electrode segment 20b includes one coated portion 26b disposed between a first coated portion 28b and a second coated portion 28b'. Each of the uncoated portions 28 may have any of the sizes (e.g., surface areas or percentage lengths) described above with respect to FIGS. 1-7. Alternatively, the total size (e.g., surface area or percentage length) of uncoated portions 28b and 28b' may be the sizes described above with respect to FIGS. 1-7.

The first defibrillation electrode segment 20a is completely coated (as represented by reference number 26a). The distal portion 90 of lead body 92 also includes discrete electrode 34 located proximal to the first defibrillation electrode segment 20a. In some instances, the distal portion 90 also includes a discrete tip electrode 36 located distal to the second defibrillation electrode segment 20b. However, the distal portion 90 of lead body 92 may include more or fewer discrete electrodes arranged in any of the manners described above with respect to FIGS. 1-7. For example, one or more discrete electrodes 34 may be located between defibrillation electrode segments 20.

In another embodiment, the second defibrillation electrode segment 20b may include more than one coated portion 26 and/or more or fewer than two uncoated portions 28. For example, the second defibrillation electrode segment 20b may include a single uncoated portion 28 disposed between two coated portions 26. In a further embodiment, the first defibrillation electrode segment 20a may include the coated and uncoated portions described above and the second defibrillation electrode segment 20b may be fully coated.

In the examples illustrated in FIGS. 8 and 9, all uncoated portions 28 of a defibrillation electrode segment 20 (e.g., uncoated portions 28a and 28a' of segment 20a or uncoated portions 28b and 28b' of segment 20b) would function together since they are on the same conductive electrode. However, in instances in which the defibrillation electrode segments 20a and 20b are coupled to separate conductors the uncoated portions 28b and 28b' of segment 20b may be utilized independently of the uncoated portions 28a and 28a' of segment 20a as part of an electrode vector between one or more other electrodes, which may include the housing electrode 33.

Figure 10:
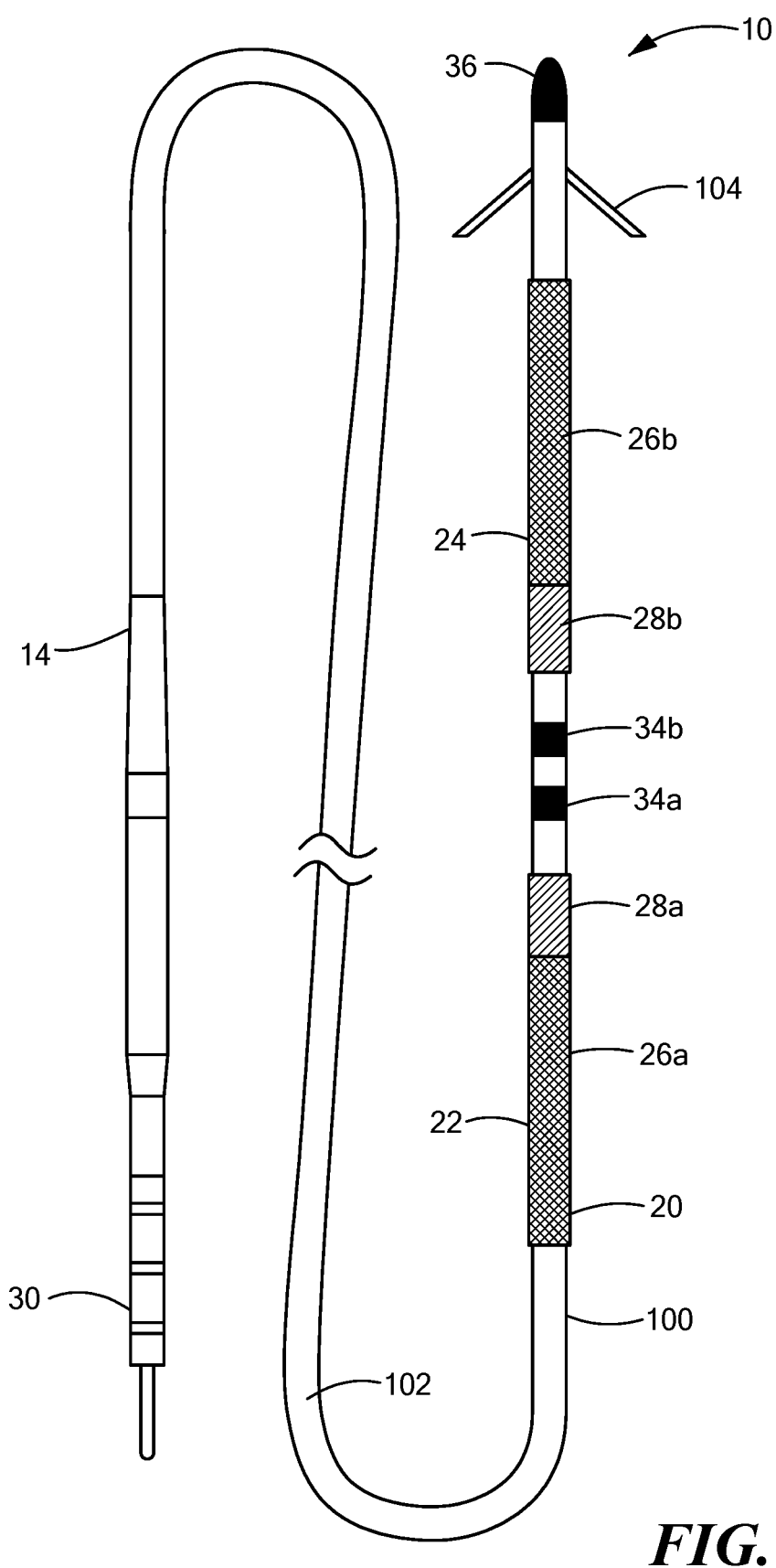
FIG. 10 is a front view of another embodiment of an extravascular medical electrical lead constructed in accordance with the principles of the present application.

FIG. 10 illustrates another configuration of a distal portion 100 and a lead body 102. Lead body 102 can include one or more of the structure and/or functionality of lead body 12 of FIGS. 1-3 (and vice versa), lead body 42 of FIG. 4 (and vice versa), lead body 52 of FIG. 5 (and vice versa), lead body 62 of FIG. 6 (and vice versa), the lead body 72 of FIG. 7 (and vice versa), the lead body 82 of FIG. 8 (and vice versa), and/or the lead body 92 of FIG. 9 (and vice versa), including the dimensions, materials, and the like. In the example illustrated in FIG. 10, lead body 102 conforms substantially to lead body 12 of FIG. 3, except lead body 102 includes an anchoring mechanism 104 and a different configuration of discrete electrodes.

Anchoring mechanism 104 is a barb or tine mechanism configured to attach to the fascia proximate the upper sternum area or to tissue underneath the sternum. However, any anchoring mechanisms may be used in place of anchoring mechanism 104. Alternatively or additionally, the anchoring mechanism 104 may be located at other locations along lead body 102 and may be affixed at one or more positions between the xiphoid process and the higher sternal area. For example, the anchoring mechanism 104 may be located proximal to the first defibrillation electrode segment 20*a*, for example, proximate to where the lead transitions from its parasternal position near the xiphoid process to its subcutaneous path laterally along the torso toward the ICD 32 (FIG. 1). Another example anchoring mechanism is described in U.S. patent application Ser. No. 14/283,278, filed Apr. 28, 2014, entitled "IMPLANTABLE MEDICAL DEVICES, SYSTEMS AND COMPONENTS THEREOF," the entirety of which is incorporated herein by reference. In other examples, the distal portion of lead body 102 may not include any anchoring mechanism 104. The one or more anchoring mechanisms 104 of lead body 102 may be the same or different from one another.

Distal portion 100 of lead body 102 includes discrete electrodes 34*a*, 34*b*, and 36. These electrodes may include the types, spacings, sizes, or other features described in any of the embodiments above. Moreover, various electrode vectors formed by the coated portions 26 and/or uncoated portions 28 of defibrillation electrode segments 20, and/or the discrete electrodes 34*a*, 34*b*, and 36, and/or the housing electrode 33 (such as of the vectors described above in FIGS. 1-9) may be utilized to deliver electrical stimulation therapy and/or sense electrical activity of the heart.

While not depicted in FIGS. 1-10 for sake of brevity, additional locations for electrodes 34 and/or 36 with respect to the positions of defibrillation electrode segments 20 are possible. For example, electrodes 34*a* and 34*b* may be positioned distal to defibrillation electrode segments 20*a* and 20*b*, respectively. In all instances, fewer or additional electrodes 34 and/or 36, not depicted, may be present distal to and/or proximal to and/or between defibrillation electrode segments 20 for every example (FIGS. 1-10). Further, more than two defibrillation electrode segments 20 may be present, with any number of electrodes 34 and/or 36 located between, proximal to and/or distal to any defibrillation electrode segments 20. For example, although in the example illustrated in FIGS. 1-3 no electrodes are located between defibrillation electrode segments 20*a* and 20*b*, an additional electrode or electrodes may be added between defibrillation electrode segments 20*a* and 20*b*, proximal to defibrillation electrode segment 20*a* and/or distal to defibrillation electrode segment 20*b* while electrodes 34 and 36 are retained as depicted.

Further, for all examples provided (FIGS. 1-10), the number of electrodes 34 or 36 depicted may be reduced. For example, although in the example illustrated in FIG. 3 two electrodes 34 and 36 are shown, one or both of electrodes 34 and 36 may be absent. For all embodiments, the type, size, shape and material of all electrodes may be the same or differ from one another. Further, the position of electrodes 34 and 36 may vary with respect to the location of uncoated and coated portions 28 and 26 or any additional or lesser number of uncoated and coated portions 28 and 26 not depicted, such that for all possible positions of electrodes 34 and 36, the uncoated or coated portions 28 and 26 may occur at the distal ends, the proximal ends, in the middle of a defibrillation electrode segment 20 or a mixture of proximal, distal and middle locations on defibrillation electrode segments 20.

In an exemplary implantation of lead body 12 of FIGS. 1-3, lead body 42 of FIG. 4, lead body 52 of FIG. 5, lead body 62 of FIG. 6, the lead body 72 of FIG. 7, the lead body 82 of FIG. 8, and/or the lead body 92 of FIG. 9, and/or the lead body 102 of FIG. 10, one or more of the uncoated portions 28 of the first defibrillation electrode segment 20*a* and/or the second defibrillation electrode segment 20*b* may be positioned subcutaneously or substernally over any desired chamber or region of the patient's heart. For example, the distal portion of any one of the lead bodies 12, 42, 52, 62, 72, 82, 92, or 102 may be positioned subcutaneously or substernally over the cardiac silhouette, as seen under anterior-posterior fluoroscopy, such that one or both the uncoated portions 28 of the defibrillation electrode segments 20 are positioned subcutaneously or substernally substantially over a ventricle or other cardiac target. In one instance, the distal portion of any one of the lead bodies 12, 42, 52, 62, 72, 82, 92, or 102 may be positioned subcutaneously or substernally over the cardiac silhouette, as seen under anterior-posterior fluoroscopy, such that the insulated portion between the defibrillation electrode segments 20 is substantially centered over a ventricle or other cardiac target.

As such, this disclosure further contemplates a method that includes creating an incision at a first location proximate a center of a torso of the patient, introducing an implant tool into the patient through the incision at the first location, advancing a distal end of the implant tool to create a tunnel, introducing the medical electrical lead into the tunnel such that the distal portion of the elongate lead body is positioned in any of the locations described above. For example, the distal portion of the elongate lead body may be positioned between a first position proximate the xiphoid process and a second position superior to the xiphoid process such that at least one of the plurality of the defibrillation electrode segments is positioned anterior over a chamber of the heart. In one example, the tunnel may be a subcutaneous tunnel through subcutaneous tissue and/or muscle above the ribcage. In another example, the tunnel may be a substernal tunnel through tissue, lymph vessels, lymph glands, substernal musculature, or other anatomical structures in the substernal space. In other instances, the tunnel may be formed by advancing the implant tool through an incision near the manubrium to form a tunnel inferior toward the xiphoid process.

In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An implantable medical electrical lead comprising:
   an elongate lead body having a proximal end and a distal portion;
   a first electrode on the distal portion of the elongate lead body, wherein the first electrode comprises:
   a first segment comprising at least one coated portion which is coated with an electrically insulating material configured to:
   attenuate transmission of a pacing pulse to a heart of a patient; and allow transmission of a defibrillation shock to the heart of the patient; and a second segment which is separated from the first segment by a distance, wherein the second segment comprises:
at least one coated portion which is coated with the electrically insulating material; and
at least one uncoated portion configured to:
transmit a pacing pulse to the heart of the patient; and
sense the electrical activity of the heart,
wherein the electrically insulating material is configured to increase attenuation of sensing of electrical activity of the heart by the at least one coated portion compared to the at least one uncoated portion; and a second electrode on the distal portion of the lead body, wherein the second electrode is configured to:
deliver one or more pacing pulses the heart; and
sense the electrical activity of the heart.

2. The lead of claim 1, wherein the electrically insulating material is tantalum pentoxide.

3. The lead of claim 1, wherein the second electrode is disposed on the elongate lead body proximal to the first electrode.

4. The lead of claim 1, further comprising an electrical conductor disposed within the elongate lead body, wherein the first segment of the first electrode is electrically connected to the electrical conductor, and wherein the second segment of the first electrode is electrically connected to the electrical conductor.

5. The lead of claim 1, further comprising:
a first electrical conductor disposed within the elongate lead body, wherein the first segment of the first electrode is electrically connected to the first electrical conductor; and
a second electrical conductor disposed within the elongate lead body, wherein the second segment of the first electrode is electrically connected to the second electrical conductor.

6. The lead of claim 5, further comprising a third electrical conductor disposed within the elongate lead body, wherein the second electrode is electrically connected to the third electrical conductor.

7. The lead of claim 1, wherein the first segment of the first electrode further comprises at least one uncoated portion configured to perform any one or more of:
transmit one or more pacing pulses to the heart of the patient; or
sense electrical activity of the heart.

8. The lead of claim 7, wherein the at least one uncoated portion of the first segment comprises one uncoated portion located at a distal end of the first segment, and wherein the at least one coated portion of the first segment comprises one coated portion located proximal to the one uncoated portion of the first segment.

9. The lead of claim 1, wherein the first segment of the first electrode is disposed on the elongate lead body proximal to the second segment of the first electrode, and wherein the second electrode is disposed on the elongate lead body between the first segment of the first electrode and the second segment of the second electrode.

10. The lead of claim 1,
wherein the lead further comprises a third electrode on the distal portion of the lead body,
wherein the third electrode is configured to perform one or both of:
deliver one or more pacing pulses the heart; or
sense the electrical activity of the heart, and
wherein the third electrode is disposed on the elongate lead body distal to the second segment of the first electrode.

11. An implantable medical electrical lead comprising:
an elongate lead body having a proximal end and a distal portion;
a first electrode on the distal portion of the elongate lead body, wherein the first electrode comprises:
a first segment comprising at least one coated portion which is coated with an electrically insulating material configured to:
attenuate transmission of one or more electrical signals which include a voltage magnitude of less than a first voltage magnitude value; and
allow transmission of one or more electrical signals which include a voltage magnitude of greater than a second voltage magnitude value, wherein the second voltage magnitude value is greater than or equal to the first voltage magnitude value; and
a second segment which is separated from the first segment by a distance, wherein the second segment comprises:
at least one coated portion which is coated with the electrically insulating material; and
at least one uncoated portion configured to allow transmission of one or more electrical signals which include a voltage magnitude of less than the first voltage magnitude value,
wherein the electrically insulating material is configured to increase attenuation of sensing of the electrical activity of the heart by the at least one coated portion compared to the at least one uncoated portion by increasing attenuation of electrical activity of a heart by the at least one coated portion compared to the at least one uncoated portion, wherein the electrical activity of the heart includes a voltage magnitude of less than the first voltage magnitude value; and
a second electrode on the distal portion of the lead body, wherein the second electrode is configured to allow transmission of one or more electrical signals which include a voltage magnitude of less than the first voltage magnitude value.

12. The lead of claim 11, wherein the first voltage magnitude value is within a range from 1 Volt (V) to 15V, and wherein the second voltage magnitude value is within a range from 10 V to 150 V.

13. The lead of claim 11, wherein the electrically insulating material is tantalum pentoxide.

14. The lead of claim 11, wherein the second electrode is disposed on the elongate lead body proximal to the first electrode.

15. The lead of claim 11, further comprising an electrical conductor disposed within the elongate lead body, wherein the first segment of the first electrode is electrically connected to the electrical conductor, and wherein the second segment of the first electrode is electrically connected to the electrical conductor.

16. The lead of claim 11, further comprising:
a first electrical conductor disposed within the elongate lead body, wherein the first segment of the first electrode is electrically connected to the first electrical conductor; and a second electrical conductor disposed within the elongate lead body, wherein the second segment of the first electrode is electrically connected to the second electrical conductor.

17. The lead of claim 16, further comprising a third electrical conductor disposed within the elongate lead body, wherein the second electrode is electrically connected to the third electrical conductor.

18. The lead of claim 11, wherein the first segment of the first electrode further comprises at least one uncoated portion configured to allow transmission of one or more electrical signals which include a voltage magnitude of less than the first voltage value.

19. The lead of claim 18, wherein the at least one uncoated portion of the first segment comprises one uncoated portion located at a distal end of the first segment, and wherein the at least one coated portion of the first segment comprises one coated portion located proximal to the one uncoated portion of the first segment.

20. The lead of claim 11, wherein the first segment of the first electrode is disposed on the elongate lead body proximal to the second segment of the first electrode, and wherein the second electrode is disposed on the elongate lead body between the first segment of the first electrode and the second segment of the second electrode.

* * * * *